United States Patent [19]

Greenspan

[11] 4,202,769
[45] May 13, 1980

[54] METHOD FOR SEPARATING SERUM OR PLASMA FROM THE FORMED ELEMENTS OF BLOOD

[76] Inventor: Donald J. Greenspan, 235 Pavilion Ave., Riverside, N.J. 08075

[21] Appl. No.: 963,298

[22] Filed: Nov. 24, 1978

Related U.S. Application Data

[63] Continuation of Ser. No. 807,013, Jun. 16, 1977, abandoned.

[51] Int. Cl.$^2$ ............................................. B01D 21/26
[52] U.S. Cl. ...................................... 210/83; 210/516; 210/DIG. 23
[58] Field of Search ................. 137/DIG. 4, 843, 859, 137/541, 493.4; 210/77, 78, 172, 83, 84, 117, 136, 313, 329, 359, 398, 420, 429–432, 516, 532 R, 533, 538, DIG. 23, 514, 515, 518; 233/1 A

[56] References Cited

U.S. PATENT DOCUMENTS

| | | | |
|---|---|---|---|
| 1,777,408 | 10/1930 | Hunicke | 210/172 |
| 2,191,636 | 2/1940 | Walker | 137/493.4 |
| 3,227,173 | 1/1966 | Bernstein | 137/859 |
| 3,661,265 | 5/1972 | Greenspan | 210/DIG. 23 |
| 3,799,342 | 3/1974 | Greenspan | 210/83 |
| 3,891,553 | 6/1975 | Ayres | 210/DIG. 23 |
| 3,894,951 | 7/1975 | Ayres | 210/DIG. 23 |
| 3,894,952 | 7/1975 | Ayres | 210/DIG. 23 |
| 3,954,614 | 5/1976 | Wright | 210/DIG. 23 |
| 3,962,086 | 6/1976 | Liston et al. | 210/DIG. 23 |

*Primary Examiner*—Frank Sever
*Attorney, Agent, or Firm*—Woodcock, Washburn, Kurtz, Mackiewicz & Norris

[57] ABSTRACT

A self-contained separator assembly comprises a container having at least one end open which is adapted to receive blood for subsequent separation into a light phase comprising plasma or serum and a heavy phase comprising the formed elements of blood. A closure is sealed into the open end of the container which may be penetrated by a cannula through which blood may be received into the container. A piston-like plug which forms a seal against the container wall is characterized by an average specific gravity so as to permit the plug to be centrifuged through a blood sample toward the interface of the heavy phase and the light phase. The plug comprises a valve seating portion having a valve opening therein and a valve head adapted to seat on the seating portion and bias means extending between the seating portion and the valve head to bias the head to the seated position on the seating portion after centrifugation.

8 Claims, 5 Drawing Figures

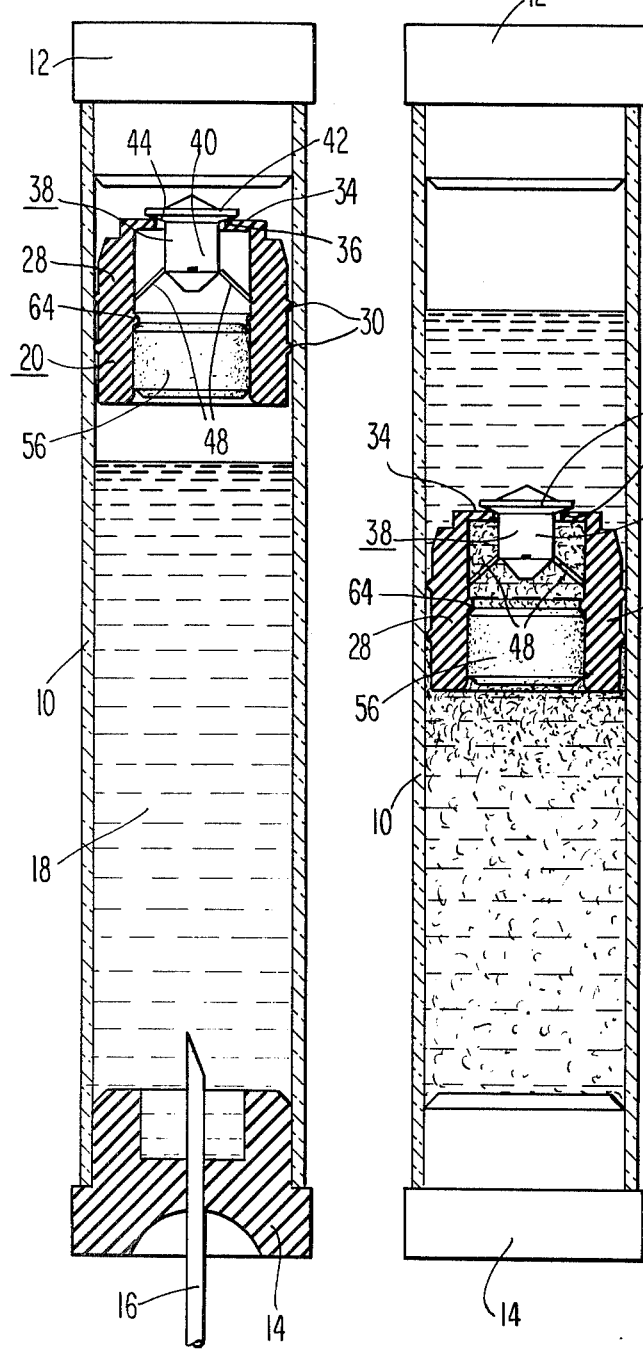
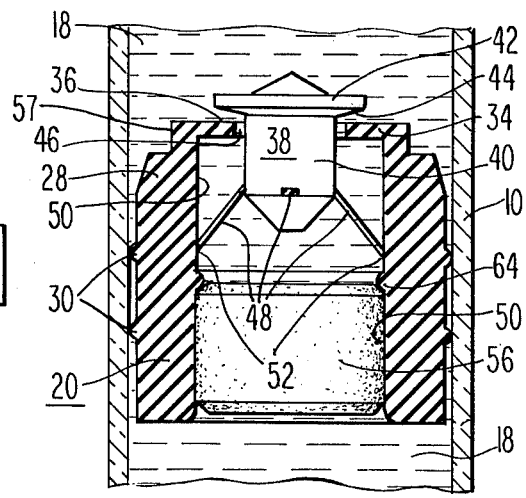
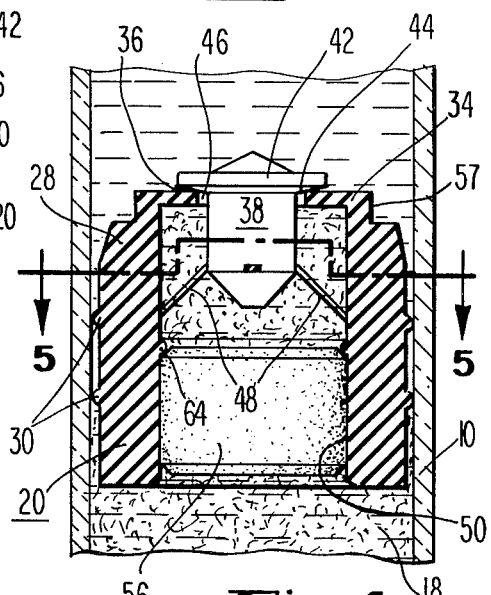
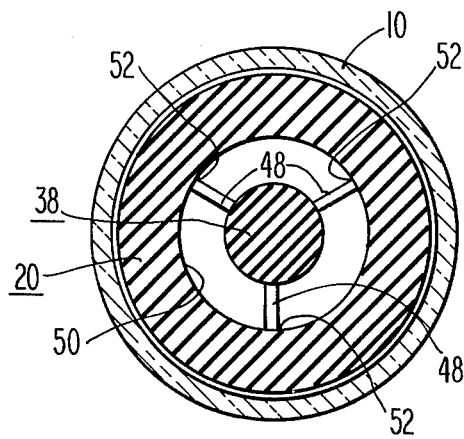
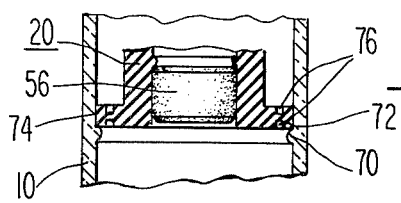

4,202,769

METHOD FOR SEPARATING SERUM OR PLASMA FROM THE FORMED ELEMENTS OF BLOOD

This is a continuation of application Ser. No. 807,013, filed June 16, 1977, now abandoned.

BACKGROUND OF THE INVENTION

This invention relates to the separation of the formed elements or the heavy phase of a blood sample, i.e., white cells, red cells and platelets of blood, from the serum or plasma or the light phase of the blood.

Such separation is typically performed by centrifuging a blood sample so that the heavier phase is forced to one end of the blood sample and the lighter phase is forced to the other end of the blood sample.

After such separation by centrifugation, it is desirable to physically separate the formed elements of the blood from the serum or plasma in order to prevent the contamination of the serum or plasma. Such contamination can occur as the red blood cells begin to liberate potassium and other contaminants which might interfere with tests performed on the serum or plasma. It is also possible that any fibrum which remains in the sample may produce some contamination.

In order to achieve this isolation or fluid separation of the formed elements of the blood from the serum or plasma, self contained separator assemblies of the Vacutainer type have been suggested. Examples of such Vacutainer assemblies are shown in U.S. Pat. Nos. 3,891,553, 3,894,951 and 3,894,952.

Such blood separation apparatus typically comprises a collection container having elastomeric plugs sealing opposite ends of the container with a piston-like plug located within the container and forming a seal with the walls of the container. A partial vacuum is created on the interior of the container so as to assist in drawing the blood sample into the container through a cannula which penetrates one of the end plugs. The plug which is characterized by an average specific gravity greater than the light phase of the blood comprises a pressure-responsive valve which, under the force of centrifuging and the pressure of serum or plasma against the valve, will open the valve to allow the plasma or serum to pass therethrough. The plug typically also comprises a filter member associated with the valve to prevent fibrin or formed elements of the blood from clogging or passing through the valve. As centrifugation continues, the plug will stop at the interface between the light phase and the heavy phase as the filter becomes clogged with the elements of the heavy phase. Once centrifugation is completed, the light phase should be on one side of the plug and the heavy phase should be on the other side of the plug.

Reliance on the clogged filter to stop the plug at the interface of the light phase and the heavy phase can result in lysing of the blood cells due to the pressure placed on the cells by the clogged filter. Once lysing occurs, any contact between the lysed cells and the serum or plasma will produce contamination of the serum or plasma.

It has been found to be particularly desirable to utilize the separator assembly in and of itself as a transport apparatus for transporting the blood sample to the laboratory from the point at which the blood sample is taken. This requires the valve of the assembly to close tightly after centrifugation and remain closed so as to prevent any contamination between the two phases of the blood.

Heretofore, valves of self-contained separator assemblies have in general relied upon the elastomeric properties of the plug or valve to return the valve to the closed condition, i.e., there is no force or bias acting on the valve after centrifugation to hold the valve closed. Rather, the valve elements, when properly structured, merely contact one another when returning to a natural or unbiased state. Closure of these valves may be assisted by the tubular member of the container if the inside diameter of the tubular member is slightly smaller than the outside diameter of the plug but the tolerances on the inside diameter of the tubular member are difficult to control particularly where the tubes are extruded.

A further difficulty associated with such separator apparatus is a result of the necessity for the valve to open with the force generated during centrifugation and still close after centrifugation.

Similar characteristics may be found in the valve structures of my U.S. Pat. Nos. 3,661,265 and 3,799,342 where plunger type serum separators are adapted to serve as transport devices. U.S. Pat. No. 3,954,614 also discloses a valve in a serum separator which is characterized by little or no seating forces when the valve is in the closed position. The same is true with respect to U.S. Pat. No. 3,962,085 wherein the periphery of the disc acts as a valve which is closed when the disc is in the closed position. However, there are no substantial seating forces beyond the weight of the blood sample itself. Valves such as those shown in U.S. Pat. Nos. 1,777,408 and 2,191,636 are biased so as to provide a substantial seating force when in the closed position, but such valves are too complex for use in serum separators.

SUMMARY OF THE INVENTION

It is an object of this invention to provide a self-contained separator assembly with an improved valve and a method of operating the assembly.

It is a more specific object of this invention to provide such a separator assembly with a valve which will maintain itself in the closed or seated position after centrifugation.

It is another specific object of this invention to provide such a separator assembly with a valve which will properly open under the influence of centrifugation.

It is a further specific object of this invention to provide such a separator assembly with an improved valve which is relatively easy to manufacture.

In accordance with these and other objects of the invention, the separator assembly comprises a container having at least one open end which is adapted to receive blood for subsequent separation into a light phase and a heavy phase and a closure seated at the open end of the container. The closure comprises a material which may be penetrated by a cannula through which blood may be received into the container. A piston means having an average specific gravity permitting the piston means to move toward the interface of the heavy phase and the light phase of the blood under the influence of specific gravity comprises a peripheral sealing means and a valve means. The peripheral sealing means is adapted to sealingly engage the container wall at the periphery of the container. The valve means comprises a seating portion having an opening therein, a movable valve member adapted to seat on the seating portion and bias means coupled to the valve member and the seating portion for maintaining substantial seating forces between the seating portion and the valve member when the valve member is closed. In accordance with this invention, the valve opening is effective to allow plasma or serum to pass therethrough under the force provided during centrifugation while at the same time returning to the closed position after centrifugation with seating forces acting on the valve.

In the preferred embodiment of the invention, the bias means comprises at least one flexible strand of elastomeric material which extends from the valve member on the under side of the valve opening to an anchoring location on the valve seating portion. In the closed position, the valve strand is maintained under tension so as to hold the valve member in the closed position. As the plasma or serum pushes against the valve member during centrifugation, the flexible strand stretches and the valve member becomes unseated so as to allow the plasma or serum to flow through the valve opening. After centrifugation, the tension on the flexible strand returns the head to the seated position at the valve opening while the strand remains under tension so as to assure the desired closure of the valve.

In accordance with one important aspect of the invention, the valve means in integrally molded on one side of the valve opening and subsequently forced through the opening to create the tension on the strand.

In accordance with another important aspect of the invention, the valve member floats above the valve opening during centrifugation so as to be separable from the valve opening around the entire periphery thereof.

In accordance with another important aspect of the invention, the valve seating portion may comprise a cylindrical section and a seating section at one end of the cylindrical section where the seating section includes the valve opening. The flexible strand extends from the valve member through the central chamber formed by the central section and the flexible strand is anchored on the cylindrical section. Preferably a plurality of flexible strands are utilized.

In one embodiment of the invention, the piston means seeks the interface between the light phase and the heavy phase by providing an average specific gravity of the piston means than the light phase and less than the heavy phase. Preferably, the specific gravity of the piston means including a filter is 1.030 to 1.040. One preferred material for the elastomeric material which provides the desired specific gravity is Kraton with appropriate fillers. In the alternative, the specific gravity may be greater when mechanical stop means are provided.

BRIEF DESCRIPTION OF THE DRAWINGS

FIG. 1 is a sectional view of a separator assembly in accordance with this invention which has been filled with a blood sample but has not yet been centrifuged;

FIG. 2 is a sectional view of the apparatus of FIG. 1 after centrifugation;

FIG. 3 is an enlarged partial sectional view of the apparatus of FIG. 1 during centrifugation;

FIG. 4 is an enlarged sectional view of the apparatus of FIG. 1 after centrifugation; and FIG. 5 is an enlarged sectional view of the apparatus of FIG. 4 taken along line 5—5.

DETAILED DESCRIPTION OF PREFERRED EMBODIMENTS

FIG. 1 discloses a self-contained separation apparatus embodying the invention which comprises a tubular container member 10 having two open ends which are closed respectively by a first closure 12 and a second closure 14 which are seated in the open ends. Each of the closures 12 and 14 comprise a self-sealing, elastomeric material such as rubber or Kraton. As shown, closure 14 is penetrated by a cannula 16 through which blood 18 is received into the container 10. By creating a vacuum within the container 10, the blood is readily drawn into the container. Because of the elastomeric nature of the closure 14, the cannula 16 may be removed from the closure 14 with the hole automatically closing.

In accordance with this invention, the container 10 encloses a novel piston means comprising a plug 20. The plug 20 comprises a substantially cylindrical body portion 28 which carries a plurality of annular, peripheral sealing beads 30 which form a seal with the walls of the container 10. The end of the body member 28 remote from the blood sample 18 comprises a radially inwardly directed annular flange 34 which is adapted to form a valve seat along the surface 36 for a movable valve member 38. In FIG. 1 and better shown in enlarged views of FIGS. 3 and 4, the valve member 38 comprises a body portion 40 terminated by a sealing head portion 42 which is adapted to seat on the surface 36 along a surface 44 at a valve opening 46.

In order to provide a closing bias on the valve member 38 which is independent of the diameter of the container 10, resilient strand or strut members 48 are attached to the interior walls of the cylindrical body 28 of the plug 20. As shown in FIG. 5, three such strands or struts 48 may be utilized which are evenly spaced around the wall 50 and the valve member 38 at points of attachment 52 so as to assure that the appropriate seal will be formed between the sealing surface 44 and the seating surface 36 as shown in FIGS. 1, 2 and 4.

In accordance with this invention, the plug 20 is integrally molded from an elastomeric material such as Kraton. As originally molded, the head 42 is on the other side of the valve opening 46 so that there is no tension on the strands 48. However, once the head or sealing portion 42 is forced through the opening 46 as shown in FIGS. 1–4, the strands 48 are under tension and store energy so as to force the sealing surface 44 into contact with the seating surface 36 in the absence of centrifugation forces. Of course, the valve member 38 may be pushed back through the opening 46 to relieve the tension on the strands 48. The beads 30 are capable of providing a seal with the container member 10 while still providing an accommodation to variation in the internal diameter of the container member 10. In addition, an annular recess 57 is located at the flange 34 which spaces the flange 34 from the walls of the container member 10 and thereby assures that any variation in the internal diameter of the container member 10 will not adversely affect the operation of the valve member 38.

As shown in FIGS. 1–4, a filter 56 is inserted into the central cavity formed by the wall 50 of the body member 28. The purpose of the filter is to prevent fibrin and any formed elements of the blood from passing through the valve opening 44 during centrifugation. To prevent the filter 56 from riding up in the cavity formed by the wall 50, an annular projection or bead 64 is located on the wall 50 just above the filter 56. The bead 64 assures that the filter is not forced upwardly so as to interfere with the valve member 38. The filter may comprise a variety of materials having pores sufficiently smaller than the blood cellular material so as to prevent the cellular material from passing through the valve opening 46.

During centrifugation, the plasma or serum of the blood sample forces the head 42 upwardly and off the seating surface 36 so as to allow the serum or plasma to pass therethrough to achieve a light phase at the end of the container 10 adjacent the closure 12 and a heavy phase at the end of the container 10 adjacent closure 14 as shown in FIG. 2. It will be understood that the strands 48 must provide the appropriate amount of bias on the head 42 so as to permit the head 42 to lift off the seating surface 36 during centrifugation. At the same time, the strands 48 must provide sufficient bias on the head 42 to assure closure on the surface 36 after centrifugation is completed as shown in FIG. 3.

In order to assure that the plug 20 will appropriately seek the interface between the light phase and the heavy phase as shown in FIG. 2, the plug 20 must have the appropriate specific gravity. In this connection, it has been found that an average specific gravity of 1.030 to 1.040 is particularly suitable. One elastomeric material which has been found to be well suited for providing the necessary bias on the valve member 38 as well as the appropriate specific gravity for the entire plug including the filter is Kraton with appropriate fillers. It must be appreciated that other elastomeric materials with suitable specific gravities might be substituted.

In the embodiment of FIG. 6, a mechanical stop in the form of a projection 70 is used to stop the plug 20 rather than the specific gravity relied upon in FIGS. 1-5. Accordingly, the average specific gravity of the plug 20 need only be greater than the light phase, i.e., 1.030 or greater so as to be sure that the plug may be centrifuged through the plasma or serum.

In the plug of FIG. 6, an annular sealing flange 72 has been substituted for the beads 30. The flange 70 includes annular relieved areas 76 which are provided so that the flange may readily retract and extend to achieve the appropriate seal at a radially surface 74 which contacts the wall of the container 10. The remainder of the plug 20 is identical to that shown in FIGS. 1-5.

A method of making the plug 20 is disclosed in my copending application Ser. No. 793,284 filed May 3, 1977, which is incorporated herein by reference, and abandoned in favor of continuation application Ser. No. 963,298 filed Nov. 24, 1978. Reference is also made to my related copending application Ser. No. 793,282 filed May 3, 1977 which discloses a serum separator tube assembly utilizing various plugs having features incorporated herein by reference.

Although a specific embodiment of the invention has been shown and described, it will be understood that other embodiments and modifications may be utilized without departing from the true spirit and scope of the invention as set forth in the appended claims.

What is claimed is:

1. A method of separating blood into a light phase comprising plasma or serum and a heavy phase comprising the formed elements of the blood including a separator assembly comprising a container having one end and another end, said container being adapted to receive blood from subsequent separation into the light phase and the heavy phase, piston means having an average specific gravity greater than said light phase, the piston means including a container sealing means adapted to sealingly engage the container wall at the periphery of the container, a valve seating portion having a valve opening therein, said valve opening permitting serum or plasma to flow through the piston means, a movable valve member adapted to seat on the seating portion so as to close the valve opening, and bias means connected between the valve member and the valve seating portion, said method comprising the following steps:

centrifuging the formed elements of the blood toward one end of the container so as to form the heavy phase and the plasma or serum toward the other end of the container so as to form the light phase;

centrifuging the piston means through the container toward the interface of the centrifuged formed elements and the centrifuged plasma or serum;

overcoming the seating force maintained by the bias means on the valve member during centrifuging so as to open the valve opening; and maintaining a substantial seating force on the valve member through the bias means when the piston means comes to rest in the container so as to close the valve opening; said force being sufficiently great to maintain said valve member in a seated position when said valve member comes to rest in the container at the interface between said light phase and said heavy phase.

2. The method of claim 1 whrein the seating force is maintained through the application of tension on the bias means.

3. The method of claim 2 wherein the bias means comprises at least one flexible strand maintained under tension.

4. The method of claim 2 wherein said bias means comprises at least one flexible strand and said valve member comprises a head, said strand being maintained under tension so as to bias the head against the valve seating portion at the valve opening when said strand is maintained under tension and the piston means comes to rest within the container.

5. The method of claim 1 wherein the valve member comprises a head, said method including the additional step of floating said head away from said valve member during centrifuging.

6. The method of claim 5 wherein the head floats free of the valve opening around the entire periphery of the plug during centrifuging.

7. The method of claim 1 wherein the piston means comprises an average specific gravity greater than the light phase and lighter than the heavy phase, said method including the additional step of seeking said interface in response to the average specific gravity of the piston means relative to the specific gravity of the light phase and the heavy phase.

8. The method of claim 1 wherein the assembly comprises mechanical stop means, said method comprising the additional step of stopping said piston means in response to said stop means.

* * * * *

UNITED STATES PATENT AND TRADEMARK OFFICE
CERTIFICATE OF CORRECTION

PATENT NO. : 4,202,769
DATED : May 13, 1980
INVENTOR(S) : Donald J. Greenspan

It is certified that error appears in the above-identified patent and that said Letters Patent are hereby corrected as shown below:

Column 5, line 43, delete "readily" and insert therefor -- radially --.

Column 5, line 44, delete "radially" and insert therefor -- sealing.

Column 6, line 34, Claim 2, delete "whrein" and insert therefor -- wherein --.

Signed and Sealed this

Second Day of September 1980

[SEAL]

Attest:

SIDNEY A. DIAMOND

Attesting Officer     Commissioner of Patents and Trademarks